United States Patent [19]
Karakus et al.

[11] Patent Number: 5,712,710
[45] Date of Patent: Jan. 27, 1998

[54] SPECTROPHOTOMETRIC PROBE FOR INSITU MEASUREMENT

[75] Inventors: Cetin Karakus, 20 Carlton St., No. 1626, Toronto, Ontario, Canada, M5B 2H5; Leena Das, Kearny, N.J.

[73] Assignee: Cetin Karakus, Ontario, Canada

[21] Appl. No.: 729,845

[22] Filed: Oct. 15, 1996

[51] Int. Cl.$^6$ ................................................. G01N 21/59
[52] U.S. Cl. ........................... 356/436; 356/440; 250/576
[58] Field of Search ................................. 356/402, 409, 356/412, 414, 416, 436, 440, 442, 31.9; 250/226, 573, 574, 576

[56] References Cited

U.S. PATENT DOCUMENTS

| | | | |
|---|---|---|---|
| 3,319,514 | 5/1967 | McAllister, Jr. | 356/442 |
| 3,727,066 | 4/1973 | Louderback et al. | 356/436 |
| 3,734,629 | 5/1973 | Griffiths et al. | 356/440 |
| 4,719,359 | 1/1988 | Rose | 356/436 |

FOREIGN PATENT DOCUMENTS 53-88788  8/1978  Japan ........................... 356/442

*Primary Examiner*—F. L. Evans
*Attorney, Agent, or Firm*—Mirek A. Waraksa

[57] ABSTRACT

A portable, hand-held spectrophotometric probe detects the concentration of a material dissolved in a liquid bath. The probe has an elongate hollow handle with an open lower end. A transparent cylindrical cell is attached to the lower end of the handle and fills with liquid when the cell is immersed in the bath. A source of light whose spectrum includes an absorption band of the dissolved material is mounted in the handle and transmits light through the cell to a photodetector. The photodetector produces a signal indicative of the intensity of the light, and the signal is transmitted along wiring to a signal outlet in the upper end of the handle. A hand-held processing unit is coupled with a cable to the outlet to receive the signal and then calculates and displays the concentration of the dissolved material.

15 Claims, 3 Drawing Sheets

SPECTROPHOTOMETRIC PROBE FOR INSITU MEASUREMENT

FIELD OF THE INVENTION

The invention relates generally to spectrophotometric measurement, and more particularly, to portable probes and methods for in-situ measurement of the concentration of materials dissolved in liquid.

DESCRIPTION OF THE PRIOR ART

The present invention has particular, though not exclusive, application to the plating industry. Spectrophotometers are used in the plating industry to measure metal ion concentration. Such equipment commonly includes a pump which transfers liquid in a bath through tubing to and from a closed spectrophotometric cell. Light from a source with a spectrum containing an absorption band of the particular metal ion is directed through the cell and impinges on a photosensor outside the cell. The voltage produced by the photosensor in response to a constant light source is known to be related to the concentration of the active species according to Beer-Lambert's law. The concentration of the species in any particular sample can thus be calculated and displayed accordingly. There are several problems associated with such equipment: it is bulky, requires high maintenance, and is costly.

BRIEF SUMMARY OF THE INVENTION

In one aspect, the invention provides a portable hand-held spectrophotometric probe for detecting the concentration of a spectrophotometrically active material dissolved in a liquid bath. The probe comprises an elongate handle and a cell fixed to the handle and defining an open compartment that fills with liquid upon insertion into the bath. A light source mounted in the handle emits light along a transmission path that extends through the compartment and transparent sections of the cell. A photodetector is supported from the handle and located at the end of the transmission path, producing an signal indicative of the intensity of light impinging on the photodetector. In preferred form, the signal may be transmitted along wiring from the photodetector mounted proximate to a lower handle portion to a signal outlet at an upper handle portion. The voltage signal available at the outlet indicates the concentration of the material and can be monitored with any voltage-reading device. However, the probe is preferably used in combination with a hand-held processing unit coupled to the signal outlet to receive the signal and programmed to calculate and display the concentration of the material in response to the signal.

Various aspects of the invention will be apparent from a description below of a preferred embodiment and will be more specifically defined in the appended claims.

DESCRIPTION OF THE DRAWINGS

The invention will be better understood with reference to drawings in which.

DESCRIPTION OF PREFERRED EMBODIMENTS

Figure 1:
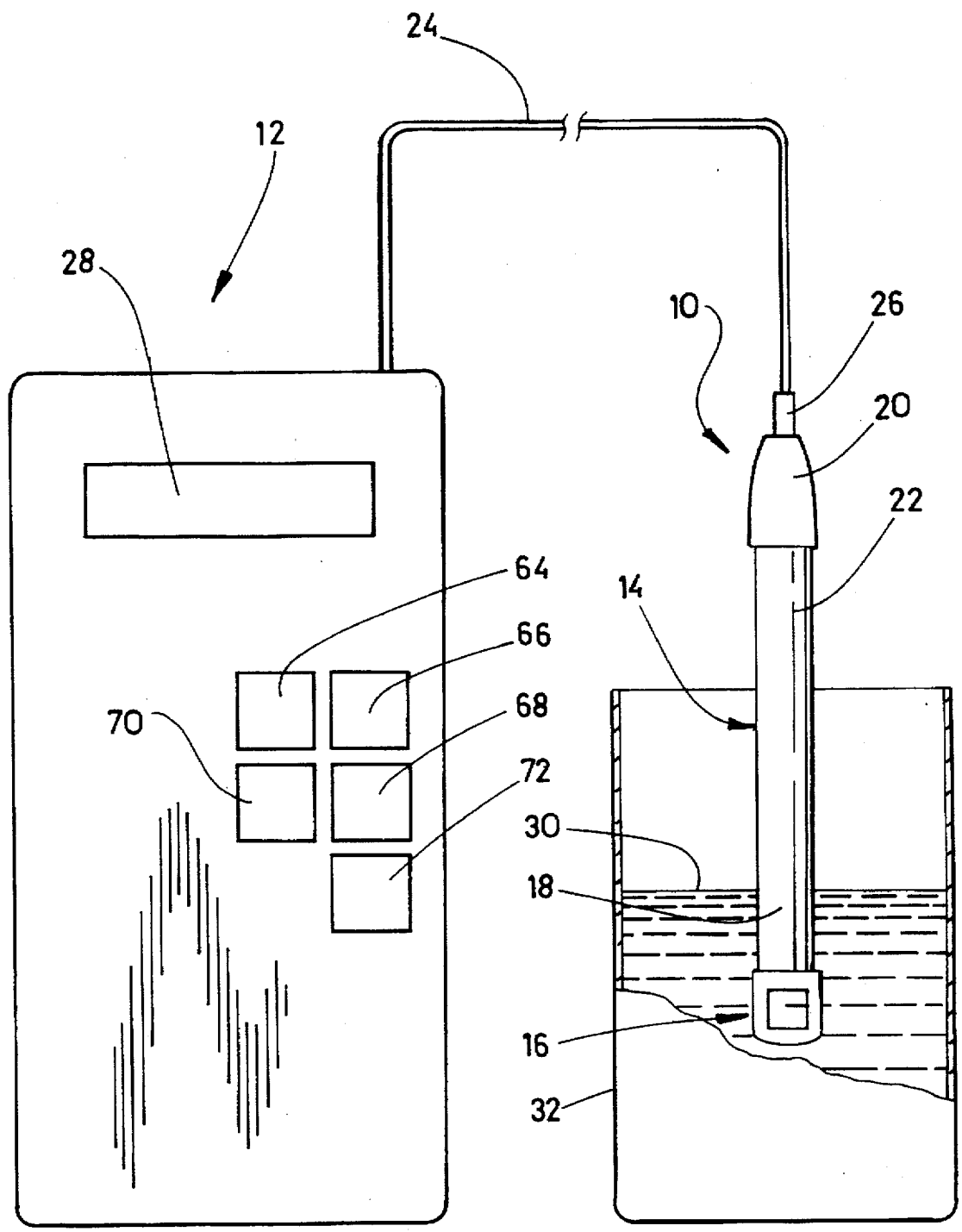
FIG. 1 is schematically illustrates a spectrophotometric probe, a processing unit, and a liquid bath in which an open cell associated with the probe is immersed.

Reference is made to FIG. 1 which illustrates a probe 10 and a processing unit 12, both of which are dimensioned to be hand-held. The probe 10 comprises an elongate/hollow handle 14 which is about the length of a conventional pencil. A spectrophotometric cell 16 is mounted to a lower portion 18 of the handle 14, and a signal outlet 20 is mounted to an upper portion 22 of the handle 14. The processing unit 12 has a cable 24 terminated with a male plug 26 that inserts into the probe's signal outlet 20 to receive a probe signal. The processing unit 12 will typically be programmed to calculate from the signal the concentration of a particular spectrophotometrically active species and to display the concentration on its liquid crystal display 28. For purposes of exemplification, that species will be assumed to be nickel ion, and the probe 10 and processing unit 12 will be described with reference to measurement of nickel ions in an electroless plating bath. The cell 16 would typically be immersed in a large plating bath to ascertain whether an adequate concentration of nickel is present. However, it has been shown immersed in nickel plating solution 30 in a small container 32, as might be done during calibration.

Figures 2, 3:
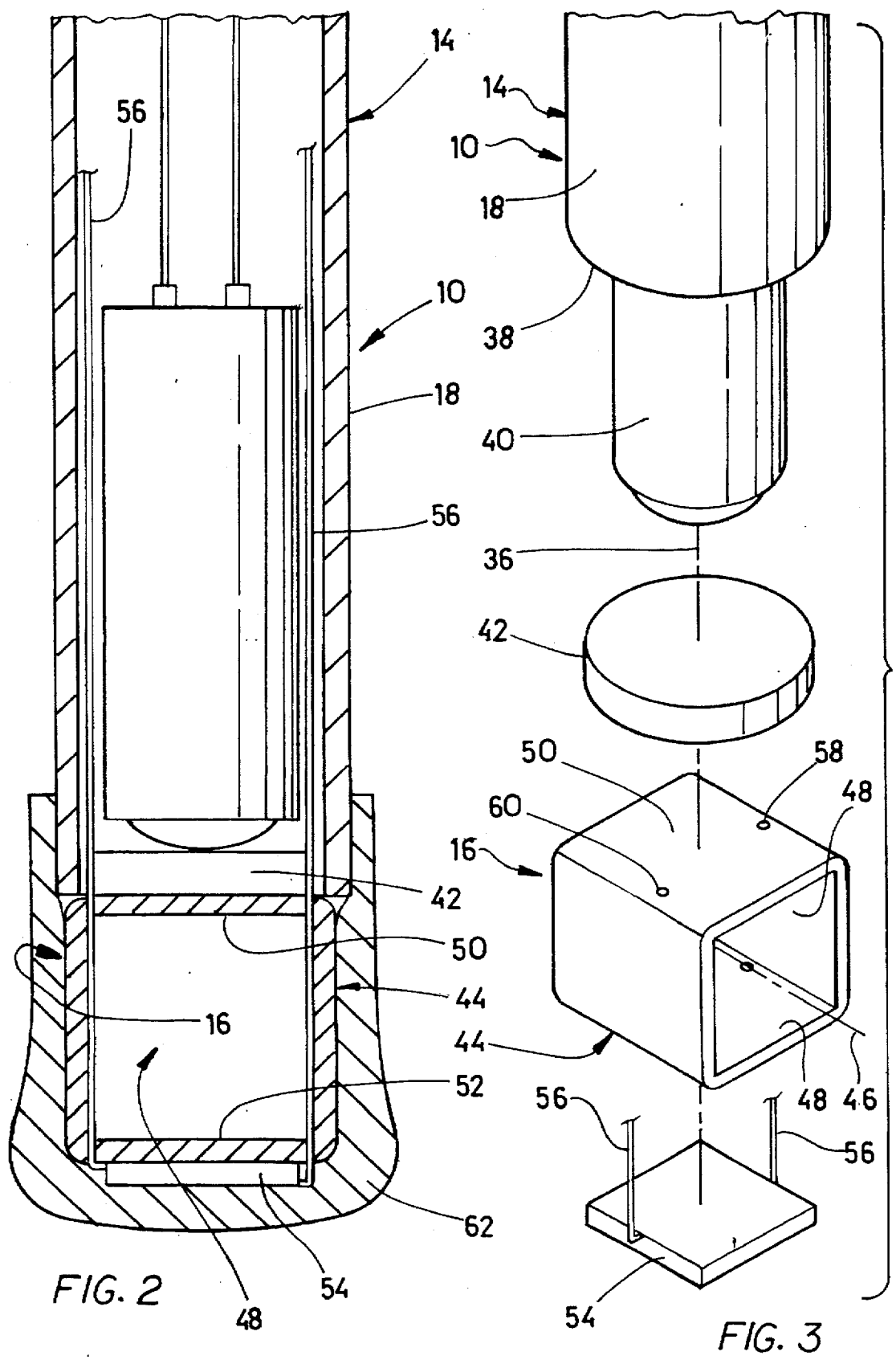
FIG. 2 is a fragmented view in partial vertical cross-section of a lower end of the probe.
FIG. 3 is an exploded perspective view of the lower end of the probe.

The construction of the probe 10 will be more apparent in FIGS. 2–3. Its handle 14 has a hollow, circular cylindrical interior 34, a central lengthwise axis 36 (the axis along which components are shown exploded in FIG. 3) and an open lower end 38. A microlaser 40 is mounted within the interior 34 and may be powered with a battery (not shown) contained in the handle 14. Alternatively, the probe 10 may be powered by a battery within the processing unit 12 and coupled with separate wires through the cable 24 to the microlaser 40. The microlaser 40 is positioned to emit light along a transmission path aligned with the lengthwise axis 36 of the handle 14. A conventional filter 42 is mounted within the handle 14 in the transmission path effectively to concentrate the spectral content of the microlaser 40 light about a particular absorption band of the nickel ion.

The cell 16 is formed of quartz which is transparent to the transmitted light. It has a generally rectangular cylindrical side wall 44 which is centered about an axis 46 transverse to the lengthwise axis 36 of the handle 14. The side wall 44 defines a compartment 48 with open ends that permit the compartment 48 to fill completely and quickly with liquid when the cell 16 is immersed in the bath. The side wall 44 has upper and lower planar wall sections 50, 52 which are transverse to and intersected by the lengthwise axis 36 of the handle 14. A conventional photodetector 54 is supported from the lower handle portion 18 and is adhered directly to the lower transparent wall section external to the compartment 48. The photodetector 54 is intersected by the lengthwise axis 36 and terminates the transmission path. In this embodiment, the transmission path is simply a straight line from the source (microlaser 40 and filter 42), through the upper transparent wall section, through the liquid within the compartment 48, and through the lower transparent wall section to the detector. The path length within the cell 16 is fixed, corresponding to the distance between the upper and lower wall sections 50, 52.

The photodetector 54 produces a voltage signal whose magnitude is proportional to the intensity of light impinging on the photodetector 54. The voltage is related by an inverse exponential relationship to the concentration of nickel ion in the liquid filling the cell 16. It should be noted that use of a laser source provides a very significant advantage of prior art devices, namely, spectrophotometrically active materials can be measured even in very high concentrations. The photodetector 54 is coupled by insulated wiring 56 to the signal port 20 to make the voltage signal accessible externally of the probe 10. The wiring 56 (two lines) extends from the photodetector 54 through narrow vertical passages (only two passages 58, 60 specifically indicated) in the upper and lower wall sections 50, 52 of the cell 16 into the open end 38 of the handle 14. The passages are spaced from the lengthwise axis 36 to avoid interference with light transmission. From the lower handle portion 18, the wiring 56 is simply directed through the interior 34 of the handle 14 to conventional terminals associated with the port 20.

Active components of the probe 10 should be protected against contact with liquids. The upper wall section of the cell 16 thus overlays the open end 38 of the handle 14 and is sealed with an adhesive to the lower handle portion 18 to prevent entry of liquids into the handle 14. The passages through the side wall 44 may be sealed with an appropriate adhesive. A sealing member 62 (specifically indicated in FIG. 2) of adhesive sealing material (such as an epoxy resin) is formed about the side wall 44 of the cell 16, sealing the photodetector 54 from direct contact with liquids. The sealing member 62 also surrounds the lower handle portion 18, further sealing its open end 38. The sealing member 62 is shaped to conform to the open ends of the cell side wall 44, leaving the compartment 48 within the cell 16 fully accessible to liquids during immersion.

The voltage signal can be used with various equipment to identify concentration. In this particular embodiment, however, the probe 10 is associated with the hand-held processing unit 12, which is pre-programmed in a conventional manner to perform simple mathematical calculations to determine nickel concentration in response to the photodetector's voltage signal. For any spectrophotometrically active species, the magnitude of the voltage will be related to the concentration of the species, as follows: $V=\beta e^{-\alpha C}$, where V is the voltage, C is the concentration of the species, and $\beta$ and $\alpha$ are constants determined mainly by the characteristics of the species (absorption), the light source (intensity and spectral content), the photodetector 54 (gain), and the dimensions of the cell 16 (path length).

Figure 4:
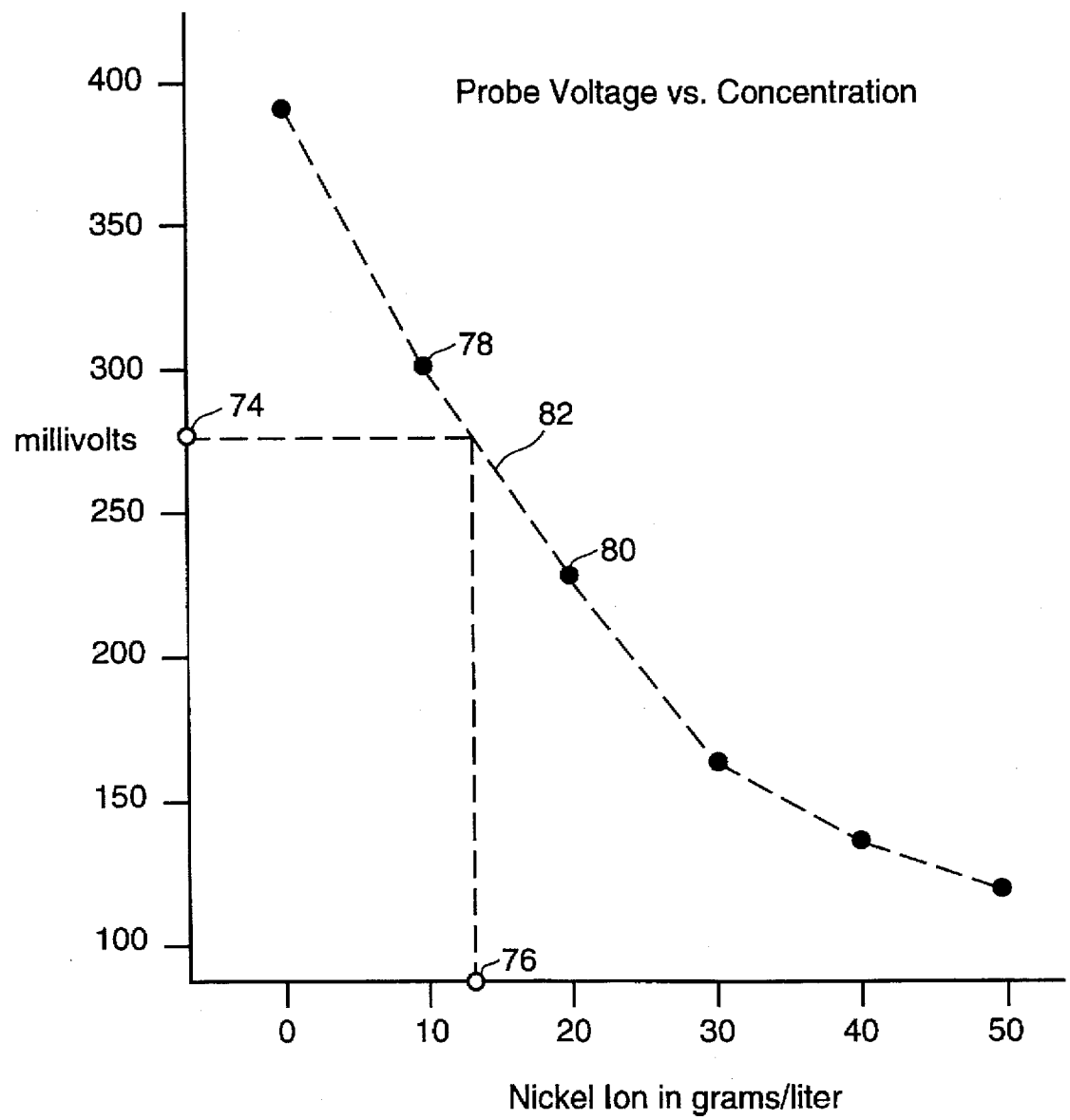
FIG. 4 is a graph relating probe voltage to nickel ion concentration.

A typical electroless nickel plating bath might typically contain 44 grams/liter nickel sulfate hexahydrate, 42 grams/liter aminoacetic acid, 10 grams/liter acetic acid, and 10 grams/liter sodium hypophosphite with pH adjusted to 4.5. To calibrate the processing unit 12, the nickel plating solution 30 may be prepared with its constituent components in such concentration but without nickel. The concentration of nickel may be increased in increments of 10 grams/liter to an upper limit of 50 grams/liter. At each step, the probe 10 is inserted into the bath and the probe voltage is measured at its signal outlet 20. Exemplary information obtained by this process is shown in the graph of FIG. 4 in which the sample points (concentration, voltage) are indicated in solid black. The sample points are stored in a conventional electronic memory associated with the processing unit 12.

The processing unit 12 is specifically programmed to have measurement and calibration modes of operation. The processing unit 12 has an assembly of push-button switches 64–72, which are labeled (labeling not illustrated): "On" (power on), "Off" (power off), "Read" (measure sample), "Exit" (terminate calibration function and otherwise clear display), and "Calibrate." The "Calibrate" switch 64 initiates the calibration mode of operation of the microprocessor associated with the processing unit 12. In the calibration mode, the processing unit 12 displays predetermined concentration values in succession on the display 28. Such displayed values might typically range from 0–100 grams/liter in increments of 10 grams/liter. The user inserts the probe 10 into a sample solution with the displayed concentration. On pressing of the "Read" switch 68, the microprocessor records the probe's voltage signal and the corresponding displayed concentration. The microprocessor then displays the next predetermined concentration value, the previous value incremented by 10 grams/liter. The user then inserts the probe 10 into the sample to which a calculated quantity of nickel ion has been added to achieve the displayed concentration, and once again presses the "Read" switch 68, causing the microprocessor to record the related voltage and concentration values. The process may be repeated until the voltage at various concentrations have been recorded, essentially accumulating the sample points illustrated in FIG. 4. Once the sample points have been accumulated, the user presses the "Exit" switch 68, and the calibration process is complete. A minimum of two sample points are required, and pressing the "Exit" switch 68 before recording two sample points terminates the calibration process.

In its measurement mode (default mode), the processing unit 12 relies on the stored sample points to calculate and display concentration values sensed by the probe 10. In this embodiment, the processing unit 12 effectively uses a piecewise straight-line approximation of the exponential curve relating the sample points (the hypothetical line segments of such an approximation being shown in phantom outline in the graph of FIG. 4) and basic interpolation to calculate concentrations. The probe 10 is inserted into a bath whose nickel ion concentration is to be measured and the probe voltage is obtained. The processing unit 10 then identifies the two stored sample points whose voltages are immediately above and below the probe voltage. For example, the probe voltage might be about 275 millivolts, indicated with a hollow circle 74 on the vertical axis of the graph of FIG. 4, which is between the voltages associated with sample points 76, 78. The corresponding concentration value (roughly 12 grams/liter) is indicated with a hollow circle 80 on the horizontal axis of the graph of FIG. 4. The two sample points 76, 78 are of course sufficient to specify the mathematical definition of the straight line which includes the line segment 82. The processing unit simply determines the parameters of the line definition from the two sample points 76, 78 and then uses the line definition to calculates the concentration value corresponding to the probe voltage. Other conventional numerical methods can of course be used to approximate the relationship between voltage and concentration, or the parameters $\beta$ and $\alpha$ of the general exponential relationship can be determined, from sample points. It should be noted that a minimum of two sample points are required and may be adequate if a narrow range of concentrations is to be measured. Using multiple sample points will provide greater accuracy. Extreme accuracy, however, is not critical in the plating industry. The programming of the processing unit 12 to perform such functions will be readily apparent from the process steps described above.

The same calibration feature can be used to calibrate the unit 12 to calculate the concentration of other active species with the probe 10. However, the filter 42 may have to be changed to accommodate absorption bands of the other species.

The transmission path in the exemplary probe 10 is simply a straight line originating at the microlaser 40, extending through the cell 16, and terminating at the photodetector 54. An alterative implementation (not illustrated)

involves mounting both the light source and the photodetector 54 in the lower portion 18 of the handle 14 and providing a reflective surface on the outer face of the transparent lower wall section to direct the transmitted light back through the cell 16 into the open end 38 of the handle 14 to the detector. The microlaser 40 may be mounted to emit light at an acute angle relative to the lengthwise axis 36 of the handle 14 or alteratively the reflective surface may be inclined relative to the lengthwise axis 36, to allow the photodetector 54 to be spaced laterally from the microlaser 40 to receive the reflected transmission. Such an arrangement requires sealing only of the lower open end 38 of the handle 14.

How the probe 10 and processing unit 12 are used and operate to measure the concentration of nickel ion a plating bath will be largely apparent from the foregoing description. However, their use will be briefly described with reference to the bath of FIG. 1. The lower handle portion 18 is immersed by hand into the solution 30 to fill the cell 16 with the liquid. Light is transmitted by the microlaser 40 through the liquid filling the cell 16 to the photodetector 54, which produces a voltage signal indicative of the intensity of the light impinging on the photodetector 54. The voltage signal is transmitted via the wiring 56 along the handle 14 to the signal outlet 20. The calibrated processing unit 12 is of course coupled to the signal outlet 20 to receive the voltage signal, and calculates the concentration of nickel as described above and displays the calculated concentration on the display 28. Unlike the prior art, no bulky equipment, pump or tubes are required. The probe 10 and processing unit 12 are also comparatively inexpensive.

It will be appreciated that a particular embodiment of the invention has been described and that modifications may be made therein without departing from the spirit of the invention or necessarily departing from the scope of the appended claims. In particular, it should be noted that the signal produced by the photodetector 54 and transmitted by wiring 56 to the probe's signal port 20 may be amplified, converted to digital form, or subjected to other conditioning within the probe 10 before being made available at the port 20. Such a conditioned signal should be understood as a signal produced by a photodetector for purposes of all claims. Also, the signal outlet may consist of a permanently wired connection from the upper portion 22 of the probe 10 to a processing unit or other equipment, rather than a connector adapted to mate with a complementary connector, or may consist of a cable extending from the upper portion 22 of the probe 10 and terminated with any appropriate connector. Although the preferred embodiment has focussed on measurement of nickel ions in order to exemplify the invention, it should be apparent that the invention can be used to detect the concentration of various spectrophotometrically active materials.

We claim:

1. A portable, hand-held spectrophotometric probe for detecting the concentration of a spectrophotometrically active material dissolved in a liquid in a liquid bath, comprising:

an elongate handle comprising hollow interior, a lengthwise axis through the interior, and an open end transverse to the lengthwise axis;

a source of light having a spectrum which includes an absorption band of the material, the light source being mounted within the handle and transmitting its light along a predetermined transmission path toward the open end of the handle;

a photodetector supported from the handle and positioned at an end of the transmission path, the photodetector producing an electrical signal indicative of the intensity of light impinging on the photodetector; and, a cell fixed to the handle, the cell comprising a generally cylindrical transparent side wall centered about an axis transverse to the lengthwise axis of the handle and sealed over the open end of the handle and cell defining a compartment with a pair of openings such that the compartment fills with the liquid upon insertion of the cell into the bath, the side wall being positioned in the transmission path and relative to the source and the detector such that the transmitted light travels a predetermined distance within the compartment before impinging on the photodetector.

2. The probe of claim 1 in which:

the photodetector is mounted to the side wall external to the compartment and is intersected by the axis;

wiring is connected to the photodetector to transmit the signal from the photodetector, the wiring extends from the photodetector through the open end of the housing; and sealing material surrounds the photodetector thereby to avoid contact between the photodetector and the liquid in the bath.

3. The probe of claim 2, in which:

the side wall of the cell comprises one planar wall section overlaying the open end of the handle at one side of the compartment and another planar wall section at an opposing side of the compartment;

the photodetector is mounted to the other planar wall section;

each of the planar wall sections is formed with passages spaced from the axis, and the wiring extends through the passages of both of the planar wall sections into the open end of the handle.

4. The probe of claim 1 in combination with a hand-held processing unit coupled to the probe to receive the signal, the processing unit programmed to calculate the concentration of the material in the liquid in response to the signal and comprising a display for displaying the calculated concentration.

5. The probe and processing unit of claim 4 in which the processing unit has a manually-operable switch and in which the processing unit is programmed to have a calibration mode of operation in which a plurality of concentration values are displayed in succession on the display and the processing unit responds to operation of the switch by associating a currently existing value of the signal with a currently displayed one of the concentration values.

6. The probe and processing unit of claim 5 in which the processing unit calculates the concentration of the material in the liquid in response to the stored signal values.

7. The probe of claim 1 in which the light source comprises a laser.

8. A portable, hand-held spectrophotometric probe for detecting the concentration of a spectrophotometrically active material dissolved in a liquid in a liquid bath, comprising:

an elongate handle comprising an upper handle portion, a lower handle portion with an open end, a hollow interior, and a lengthwise axis;

a cell fixed to the lower handle portion, the cell defining an open compartment shaped to fill with the liquid upon insertion of the cell into the bath, the cell comprising one transparent wall section intersected by the lengthwise axis and overlaying the open end of the handle at one side of the compartment and another transparent wall section intersected by the axis at an opposing side of the compartment, each of the transparent wall sections being formed with passages spaced from the axis;

a source of light which has a spectrum encompassing an absorption band of the material, the light source being mounted within the handle to transmit its light along the axis;

a photodetector for producing an electrical signal indicative of the intensity of light impinging on the photodetector, the photodetector being mounted to the other transparent wall section external to the compartment and alignment with the axis such that the light from the source impinges on the photodetector; a signal outlet in the upper handle portion; and, wiring extending along the handle and coupling the photodetector to the signal outlet, the wiring extending through passages of both of the transparent wall sections into the open end of the handle.

9. The probe of claim 8 comprising a sealing member sealed about the lower end portion of the handle and about the cell thereby to isolate the photodetector from the liquid upon insertion of the lower handle portion into the bath.

10. The probe of claim 8 in which the light source comprises a laser.

11. The probe of claim 8 in combination with a hand-held processing unit coupled to the probe to receive the signal, the processing unit programmed to calculate the concentration of the material in the liquid in response to the signal and comprising a display for displaying the calculated concentration.

12. The probe and processing unit of claim 11 in which the processing unit has a manually-operable switch and in which the processing unit is programmed to have a calibration mode of operation in which a plurality of concentration values are displayed in succession on the display and the processing unit responds to operation of the switch by storing a currently existing value of the signal and associating the stored signal value with a currently displayed one of the concentration values.

13. The probe and processing unit of claim 12 in which the processing unit calculates the concentration of the material in the liquid in response to the stored signal values.

14. In the combination of a portable hand-held spectrophotometric probe adapted to produce a signal indicative of the concentration of a spectrophotometrically active material dissolved in a liquid in a bath and a hand-held processing unit programmed to calculate the concentration of the material in response to the signal produced by the probe and to display the calculated concentration on a display comprised by the processing unit, the probe comprising an elongate handle, a source of light mounted to the handle for transmission of light along a predetermined transmission path, a photodetector mounted from the handle, and a photodetector supported from the handle and positioned at an end of the transmission path, and an open cell mounted to the handle and shaped to fill with the liquid upon insertion into the bath, the cell having transparent sections positioned in the transmission path and positioned relative to the source and the detector such that the transmitted light travels a predetermined distance within the compartment before impinging on the photodetector, the improvement in which the processing unit has a manually-operable switch and in which the processing unit is programmed to have a calibration mode of operation in which a plurality of concentration values are displayed in succession on the display and the processing unit responds to operation of the switch by associating a currently existing value of the signal produced by the probe with a currently displayed one of the concentration values.

15. The combination of claim 14 in which the processing unit calculates the concentration of the material in the liquid in response to stored signal values.

* * * * *